United States Patent [19]

Nikawitz

[11] 3,975,435
[45] Aug. 17, 1976

[54] SUBSTITUTED CINNAMANILIDES
[75] Inventor: Edward J. Nikawitz, Glen Rock, N.J.
[73] Assignee: Givaudan Corporation, Clifton, N.J.
[22] Filed: Mar. 6, 1974
[21] Appl. No.: 448,768

[52] U.S. Cl. .............................. 260/558 P; 424/324
[51] Int. Cl.[2] ........................................ C07C 103/75
[58] Field of Search ..................... 260/558 P, 558 D

[56] References Cited
UNITED STATES PATENTS
3,515,753 6/1970 Bernstein et al. ........... 260/558 P X
3,835,128 9/1974 Bracha et al. ............... 260/558 P X OTHER PUBLICATIONS
CA54:7636e, "Synthesis of Some Derivatives of Cinnamic Acid and Their Antifungal Action", Schultz et al., (1959).
*Medicinal Chemistry*, Burger, 3rd Ed., (1960), p. 72.

Primary Examiner—Daniel E. Wyman
Assistant Examiner—Thomas A. Waltz
Attorney, Agent, or Firm—Thomas Cifelli, Jr.

[57] ABSTRACT
Substituted cinnamanilides are useful as bacteriostatic agents, the cinnamanilides being characterized by the presence in the aniline moiety of at least one fluorine containing substituent and in the cinnamoyl moiety by at least one halogen and having the formula:

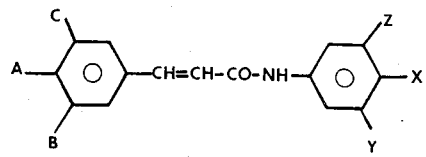

wherein:
A,B, and C are selected from the group H, Cl and Br and at least one of them is Cl or Br; X, Y and Z are selected from the group H, $CF_3$, $OCF_3$, $OCF_2CHF_2$, Cl and Br and at least one of them is $CF_3$, $OCF_3$ or $OCF_2CHF_2$; except:

when B, C and Y are all hydrogen, X cannot be hydrogen or bromine.

15 Claims, No Drawings

SUBSTITUTED CINNAMANILIDES

BACKGROUND OF THE INVENTION

1. Field of the Invention

Novel cinnamanilides as bacteriostats.

2. Description of the Prior Art

Many compounds have been suggested by the art as bacteriostatic agents in soaps, detergents and cosmetics. However, as is well known to those skilled in the art, many of these bacteriostatic compounds have some serious limitations in their use. For example, phenolic bacteriostats such as bisphenols, salicylanilides and hydroxydiphenyl ethers are photosensitive and when incorporated into a soap or detergent bar will discolor the bar upon prolonged exposure to sunlight. Bacteriostatic carbamates of bisphenols of the type disclosed in U.S. Pat. No. 3,651,128 are not photosensitive, but the cinnamanilides of this invention are far more soluble which enhances their utility in cosmetic and topical pharmaceutical preparations. Although bacteriostatic carbanilides are also not photosensitive and do not affect the whiteness of soap, each molecule can produce two molecules of aromatic amines on degradation and have the potential to provide more toxic by-products than desirable thereby limiting their use in soaps and cosmetics.

SUMMARY OF THE INVENTION

The compounds of the present invention possess the following general formula:

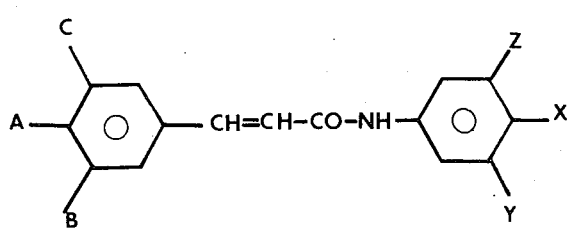

wherein:

A, B and C are selected from the group H, Cl and Br and at last one of them is Cl or Br; X, Y and Z are selected from the group H, $CF_3$, $OCF_3$, $OCF_2CHF_2$, Cl and Br and at least one of them is $CF_3$, $OCF_3$ or $OCF_2CHF_2$; except:

when B, C and Y are all hydrogen, X cannot be hydrogen or bromine.

As will hereinafter be further illustrated, compounds having chemical structures closely related to the substituted cinnamanilides of the present invention are substantially devoid of any antimicrobial activity and have no utility as bacteriostatic agents.

The substituted cinnamanilides of the present invention, exhibit in the presence of soap a minimum bacteriostatic activity of 1.25 mcg/ml against *Staph. aureus* and display little or no tendency to discolor under the influence of light. They are also soluble in aldehydes, ketones and blends of halohydrocarbons and alcohols. This solubility allows for a greater range of utility such as direct application to surface (both animate and inanimate), the permeation of various materials (.e.g. wood, paper, textiles etc.) and use in aerosols.

It is also interesting and unexpected that several of the cinnamanilides show antimicrobial activity at a dilution of one part in more than 40 million parts making them superior to the most active carbanilides. The carbanilides inhibit bacterial growth at a limit of one part in thirty million parts as reported in the literature [David J. Beaver et.al., *J. Am. Chem. Soc.*, 79, 1236 (1957)].

The substituted cinnamanilides of the present invention can be prepared by a variety of methods known in the art (e.g. Houben-Weyl, *Methoden der Organischen Chemie*, Stickstoffverbindungen, II/III, 4–14). In general, substituted cinnamanilides can be prepared by the condensation of an acid or acid derivative with an aniline derivative as shown:

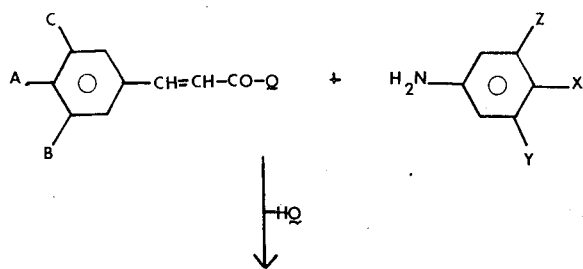

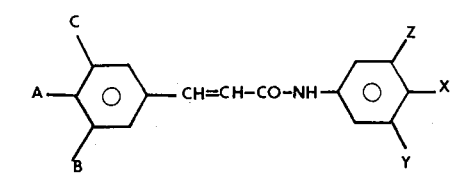

wherein:

A,B,C,X,Y and Z are as previously defined and Q is chlorine, bromine, hydroxy or alkoxy.

Various reagents are known in the art to react with HQ to aid the reaction. For example organic bases such as pyridine or excess aniline can be used to neutralize the acid formed when Q = Cl or Br. One can aid the reaction by the physical removal of HQ for example by azeotrope methods when HQ is water or an alcohol.

The preferred method for preparing the substituted cinnamanilides of the present invention involves reacting substantially equal molar amounts of an appropriately substitute cinnamoyl chloride and an appropriately substituted aniline in the presence of a suitable solvent and acid acceptor such as pyridine at a temperature of about 0° to 100°C. for time periods ranging from 1 to 30 hours.

The reaction products are precipitated from the reaction mixture by an excess of water. If the solvent used is pyridine or other alkaline solvent, it is desirable to partially or completely neutralize the solvent with an acid such as hydrochloric acid. Recrystallization of the filtered crude product may be achieved from suitable solvents as for example, toluene, toluene-hexane blends and dilute alcohols.

The substituted cinnamanilides obtained by recrysallization are crystalline, white, odorless solids which are soluble in acetone, alcohol or dimethylformamide.

The substituted cinnamanilides of the present invention may be used as anti-bacterial agents by themselves or along with a wide variety of capillary or surface-active materials besides soap. Such materials include salts of sulfated alcohols such as sodium lauryl sulfate, for example; salts of sulfated and sulfonated alkyl acids amides ("Igepon T"); salts of alkylaryl sulfonates, e.g. sodium dodecylbenzene sulfonate; alkylnaphthalenesulfonic acids and their salts ("Nekal"); salts of sulfonated alkylaryl polyether alcohols (Triton 720); and many other products, detergents and emulsifiers known to the art whether of the anionic, cationic, nonionic or amphoteric types of surface active agents. A more complete description of many of the materials included in the class of capillary active and surface active agents referred to above may be found in Encyclopedia of Surface-Active Agents, I. P. Sisley, Chemical Publishing Co., Inc., New York, and Surface Active Agents, A. M. Schwartz and I. W. Perry, Interscience Publishers, Inc., New York, New York.

As is well known, many of the available bacteriostatic agents, notably those of the quaternary ammonium salt type, are inactivated in the presence of capillary-active or surface active agents such as soaps and detergents. The bateriostatic activity of the substituted cinnamanilides of the present invention, however, as a general rule, is not substantially reduced by a wide variety of surface-active substances, and in some cases is even improved. For this reason, the substituted cinnamanilides are especially useful in combination with such capillary-active materials.

As other examples of particular applications of the substituted cinnamanilides of this invention, their use with dry powdered carriers such as starch or talcum, with or without other medicants, is noted. Incorporation into pressed solids may also be effected, if desired. Solutions of the substituted cinnamanilides of this invention in suitable solvents may be incorporated into cosmetic compositions in stick, paste, jelly, cream, lotion, roll-on, spray aerosol or other forms. The compounds of this invention can also be finely milled and incorporated into ointments by conventional techniques to render the ointments antibacterial. In addition, solutions or dispersions of the substituted cinnamanilides may also be used for cleaning medical instruments, food processing equipment, or any other surface upon which it is desired to control bacteria.

Relatively small amounts of the substituted cinnamanilides may be used in the antibacterial compositions described above, including soaps and other surface-active or detergent compositions, which may be considered to be typical as to concentration levels. Amounts as low as 0.1% to 1%, based upon the total weight of the composition may be employed although a range of about 1 to 3% is usually preferred. Amounts less than about 0.1% are generally of little value since they generally do not produce a useful degree of activity. Although 5% or more may be used, the upper limit of the amount of agent which may be used is determined by practical considerations. As a general rule, increasing the concentration of agent in the composition increases the germicidal activity of the resulting product. However, the cost of the agent relative to the cost of the product itself mitigates against the use of too large an amount of the agent. Moreover, large amounts of the agent are to be avoided if such use would adversely affect the properties of the product.

With respect to soap, the invention may be practiced by adding the agents to the soap in any suitable manner during the crushing or milling or similar operation. Care should be taken to obtain a uniform distribution of the agent throughout the soap. They may be dissolved in a small amount of a suitable solvent or may be dispersed or wetted with a suitable dispersing or wetting agent before incorporation in soap. In general, any method which results in the agent being uniformly incorporated into the final soap product is satisfactory.

The bacteriostatic compounds, as noted above, can also be incorporated in similar concentrations in cosmetic formulations and detergent compositions other than soaps, according to known techniques fully familiar to those skilled in the art. The substituted cinnamanilides of the present invention are also suitable for use in aerosols applied to animate or inanimate surfaces or for air disinfection.

A similar range of total concentration of bacteriostats can also be employed for mixtures of the substituted cinnamanilides with other bacteriostats, as for instance, bacteriostatic phenols, bisphenols, carbanilides, salicylanilides or any other bacteriostat or bactericide.

The following examples will further illustrate the invention.

EXAMPLE I

Preparation of
3,4'-Dichloro-α,α,α-trifluorocinnamo-m-toluidide

5-Amino-2-chlorobenzotrifluoride (1.8 g.) and pyridine (40 ml) were charged into a 250 ml. flask fitted with a sealed stirrer, a thermometer, a reflux condenser and a dropping funnel. Unless otherwise stated herein, the temperatures are in degrees centigrade and all parts are by weight.

An amount of 2.1 g. of m-chlorocinnamoyl chloride in dioxane (13 ml.) was added to the agitated solution over a period of 30 minutes. After being heated at 80° for 3 hours, the solution was poured into 2 l. of ice water. Concentrated hydrochloric acid (100 ml) was added. A solid precipitated and was filtered after standing for 20 hours.

The product was agitated one hour with water (100 ml) and a 10% NaOH (50 ml), filtered, and then agitated one hour with water (100 ml) and 10% HCl (50 ml).

The crude anilide obtained after filtration and drying, weighed 3.1 g. It was crystallized from a blend of hexane (40 ml) and toluene (35 ml).

Yield: 1.8 g. m.p. 128°–132°. Analysis: Calcd for $C_{16}H_{10}Cl_2F_3NO$:

|  | Calcd. | Found |
|---|---|---|
| %C | 53.4 | 53.37 |
| %H | 2.8 | 3.16 |
| %F | 15.83 | 16.03 |

EXAMPLE II

Preparation of
3-Bromo-4'-chloro-$\alpha',\alpha',\alpha'$-trifluorocinnamo-m-toluidide Following the procedure of example I, 5-amino-2-chlorobenzotrifluoride (1.5 g) was brought to reaction with 2 g. of m-bromocinnamoyl chloride in 13 ml of dioxane.

The crude material (2.5 g) was recrystallized from a blend of hexane (40 ml) and toluene (30 ml).

Yield: 1.8 g m.p. 135.5°–137° Analysis: Calcd for $C_{16}H_{10}BrClF_3NO$.

|     | Calcd. | Found |
| --- | --- | --- |
| %C  | 47.5 | 47.55 |
| %H  | 2.49 | 2.78 |
| %F  | 14.1 | 13.88 |

EXAMPLE III 3,4-Dichloro-$\alpha',\alpha',\alpha',\alpha'',\alpha'',\alpha''$-hexafluorocinnamo-3',5'-xylidide Following the procedure of example I, 3,5-di(trifluoromethyl) aniline (6.9 g) in pyridine (75 ml) was reacted with 3,4-dichlorocinnamoyl chloride (7.1 g) for 4 hours at 80°C.

The filtered product was washed as previously described, first with a mixture of water (100 ml) and 10% NaOH (75 ml) and then with a mixture of water (100 ml) and 10% HCl (75 ml).

The crude material (11.2 g) was recrystallized from a blend of hexane (50 ml) and toluene (70 ml).

Yield: 8.9 g m.p. 167°–169.5°. Analysis: Calcd for $C_{17}H_9Cl_2F_6NO$:

|     | Calcd. | Found |
| --- | --- | --- |
| %C  | 47.7 | 47.73 |
| %H  | 2.12 | 2.2 |
| %Cl | 16.6 | 16.1 |

EXAMPLE IV

Preparation of
3,4-Dichloro-$\alpha',\alpha',\alpha'$-trifluorocinnamo-m-toluidide m-Aminobenzotrifluoride (4.8 g), pyridine (60 ml) and 3,4-dichlorocinnamoyl chloride (7.1 g) were brought to reaction as described in example III.

The crude material (9.7 g) was recrystallized from toluene (70 ml).

Yield: 7.3 g m.p. 156°–158.5° Analysis: Calcd. for $C_{16}H_{10}Cl_2F_3NO$:

|     | Calcd. | Found |
| --- | --- | --- |
| %C  | 53.4 | 53.19 |
| %H  | 2.8  | 2.78 |
| %Cl | 19.7 | 19.45 |

EXAMPLE V

Preparation of
3,4,4'-Trichloro-$\alpha',\alpha',\alpha'$-trifluorocinnamo-m-toluidide 5-Amino-2-chlorobenzotrifluoride (5.9 g), pyridine (70 ml) and 3,4-dichlorocinnamoyl chloride (7.1 g) were brought to reaction as described in example III.

The crude material (11 g) was recrystallized from a blend of hexane (50 ml) and toluene (90 ml).

Yield: 7.9 g m.p. 166°–169° Analysis: Calcd. for $C_{16}H_9Cl_3F_3NO$:

|     | Calcd. | Found |
| --- | --- | --- |
| %C  | 48.6 | 49.2 |
| %H  | 2.3  | 2.38 |
| %Cl | 27.0 | 26.68 |

EXAMPLE VI

Preparation of
3-Chloro-$\alpha',\alpha',\alpha',\alpha'',\alpha'',\alpha''$-hexafluorocinnamo-3',5'-xylidide 3,5-Di(trifluoromethyl)aniline (2.1 g), pyrdine (40 ml) and m-chlorocinnamoyl chloride (2 g). in dioxane (13 ml) were brought to reaction as described in example I.

The crude material (3.2 g) was recrystallized from a blend of hexane (40 ml) and toluene (18 ml).

Yield: 1.2 g m.p. 142.5°–144.5°. Analysis: Calcd. for $C_{17}H_{10}ClF_6NO$:

|     | Calcd. | Found |
| --- | --- | --- |
| %C  | 51.9 | 52.01 |
| %H  | 2.57 | 2.82 |
| %F  | 29.0 | 28.87 |

EXAMPLE VII

Preparation of
3-Bromo-$\alpha',\alpha',\alpha'$-Trifluorocinnamo-m-toluidide m-Aminobenzotrifluoride (1.2 g), pyrdine (40 ml) and m-bromocinnamoyl chloride (1.9 g) in dioxane (13 ml) were brought to reaction as described in example I.

The crude material (2.3 g) was recrystallized from a blend of hexane (40 ml) and toluene (20 ml).

Yield: 1.5 g m.p. 134.5°–136° Analysis: Calcd for $C_{16}H_{11}BrF_3NO$:

|     | Calcd. | Found |
| --- | --- | --- |
| %C  | 51.9  | 52.6 |
| %H  | 2.99  | 3.14 |
| %Br | 21.60 | 21.42 |

EXAMPLE VIII

Preparation of
3-Bromo-$\alpha',\alpha',\alpha',\alpha'',\alpha'',\alpha''$-hexafluorocinnamo-3',5'-xylidide 3,5-Di(trifluoromethyl)aniline (1.7 g), pyridine (40 ml) and m-bromocinnamoyl chloride (1.9 g) in dioxane (13 ml) were brought to reaction as described in example I.

The crude material (2.6 g) was recrystallized from a blend of hexane (40 ml) and toluene (20 ml).

Yield: 2.2 g m.p. 140.5°–142°. Analysis: Calcd. for $C_{17}H_{10}BrF_6NO$:

|  | Calcd. | Found |
|---|---|---|
| %C | 46.7 | 46.8 |
| %H | 2.3 | 2.39 |
| %F | 26.1 | 25.99 |

EXAMPLE IX

Preparation of 3-Chloro-$\alpha'$,$\alpha'$,$\alpha'$-trifluorocinnamo-m-toluidide m-Aminobenzotrifluoride (1.5 g) pyridine (40 ml) and m-chlorocinnamoyl chloride (1.9 g) in dioxane (13 ml) were brought to reaction as described in example I.

The crude material (2.6 g) was recrystallized from a blend of hexane (40 ml) and toluene (20 ml).

Yield: 1.6 g m.p. 121°–122.5° Analysis: Calcd. for $C_{16}H_{11}ClF_3NO$:

|  | Calcd. | Found |
|---|---|---|
| %C | 59.1 | 58.89 |
| %H | 3.41 | 3.42 |
| %Cl | 10.91 | 10.66 |

EXAMPLE X

Preparation of 4,4'-Dichloro-$\alpha'$,$\alpha'$,$\alpha'$-trifluorocinnamo-m-toluidide 5-Amino-2-chlorobenzotrifluoride (5.9 g), pyridine (50 ml) and p-chlorocinnamoyl chloride (6.1 g) in dioxane (20 ml) were brought to reaction as described in example I.

The crude material (10 g) was recrystallized from alcohol (60 ml).

Yield: 5.8 g m.p. 189.5°–191°. Analysis: Calcd. for $C_{16}H_{10}Cl_2F_3NO$:

|  | Calcd. | Found |
|---|---|---|
| %Cl | 19.7 | 19.8 |

EXAMPLE XI

Preparation of 4-Chloro-$\alpha'$,$\alpha'$,$\alpha'$,$\alpha''$,$\alpha''$,$\alpha''$-hexafluorocinnamo-3',5'-xylidide 3,5-(trifluoromethyl)aniline (6.9 g), pyridine (50 ml) and p-chlorocinnamoyl chloride (6.1 g) in dioxane (20 ml) were brought to reaction as described in example I.

The crude material (10.9 g) was recrystallized from alcohol (75 ml).

Yield: 7.8 g m.p. 178°–179.5°. Analysis: Calcd. for $C_{17}H_{10}ClF_6NO$:

|  | Calcd. | Found |
|---|---|---|
| %Cl | 9.04 | 9.15 |

EXAMPLE XII

Preparation of 4'-Bromo-3,4-dichloro-$\alpha'$,$\alpha'$,$\alpha'$-trifluorocinnamo-m-toluidide 5-Amino-2-bromobenzotrifluoride (7.2 g), pyridine (50 ml) and 3,4-dichlorocinnamoyl chloride (7.g) in dioxane (24 ml) were brought to reaction as described in example I.

The crude material was recrystallized from a blend of hexane (40 ml) and toluene 90 ml).

m.p. 175°–177.5° Analysis: Calcd. for $C_{16}H_9BrCl_2F_3NO$:

|  | Calcd. | Found |
|---|---|---|
| %C | 43.8 | 43.91 |
| %H | 2.07 | 2.33 |
| %F | 13.0 | 13.26 |

EXAMPLE XIII

Preparation of 3,4-Dichloro-4'-(trifluoromethoxy)cinnamanilide p-Aminophenyl trifluoromethyl ether (0.7 g) pyridine (30 ml) and 3,4-dichlorocinnamoyl chloride (1 g) in dioxane (5 ml) were agitated and heated 3 hours at 80°–90° in a suitable flask fitted with a reflux condenser. The reaction mixture was then poured into 2 l. of ice-water containing conc. hydrochloric acid (50 ml). The crude product was filtered, washed with water and dried. It was recrystallized first from a blend of toluene (50 ml) and hexane (60 ml) and then from toluene (16 ml) and hexane (60 ml).

Yield: 0.7 g m.p. 113°–114.5°

EXAMPLE XIV

Preparation of 3,4-Dichloro-3'-(1,1,2,2-tetrafluoroethoxy)cinnamanilide 3-(Tetrafluoroethoxy)aniline (8.4 g), pyridine (50 ml) and 3,4-dichlorocinnamoyl chloride (9.4 g) in dioxane (32 ml) were brought to reaction as described in example I.

The crude anilide obtained by filtration and drying weighed 12.1 g. It was recrystallized from a blend of hexane (50 ml) and toluene (40 ml) in the presence of Filtrol No. 20.

Yield: 9.3 g m.p. 111°–114° Analysis: Calcd. for $C_{17}H_{11}Cl_2F_4NO_2$

|  | Calcd. | Found |
|---|---|---|
| %C | 50.0 | 50.05 |
| %H | 2.71 | 2.87 |
| %F | 18.65 | 18.85 |

EXAMPLE XV

The antibacterial properties of the compounds prepared in Examples I – XIV were tested in soap. The in vitro soap bacteriostatic tests were conducted as follows: The compound is dissolved in a suitable solvent, usually dimethylformamide, to give a 6% solution. One-half ml. aliquot was added to 100 ml. of 3% solution of bar soap stock solution. The solid soap used was a neutral white toilet soap to the "Lux" type. The fatty acids in this soap were of the following composition:

|  | Percent |
| --- | --- |
| Oleic and Linoleic acids | about 45 |
| Palmitic acid | about 10 |
| Lower fatty acids (lauric, etc.) | about 15 |
| Stearic acid | about 30 |

This yields an aqueous soap solution containing 30,000 mcg./ml. soap and 300 mcg./ml. compound. The soap/compound ratio in the latter is 100/1. A two fold serial dilution series is prepared with this solution using sterile distilled water in test tubes such that the final volume in each tube is 2.0 ml. To each test tube is added 28 ml. of molten Dextrose Trypticase Extract Agar (B.B.L.) The tube contents were poured into sterile Petri plates and allowed to harden. The highest final concentration of compound in the serial dilution series is 20 mcg./ml. Plates were spot inoculated with a broth culture of Staphylococcus aureus and incubated at 35° for 48 hours. The lowest concentration completely inhibiting growth of the test organism, in mcg./ml. is recorded as the bacteriostatic concentration of the compound. Tests in the absence of soap are made in a similar manner except that all dilutions are made in solvent. The highest concentration tested was 1920 mcg./ml.

The results of these tests with the compounds of the present invention as compared with compounds having chemical structures closely related to the compounds of the present invention (designated by the symbol C) are set forth in the Table. Column 1 contains the data as to the activity of the test solution without soap; column 2 refers to tests in which the ratio of soap to compound is 100:1. In both cases the numbers mean minimum concentration (mcg./ml.) where S. aureus growth is completely inhibited. Growth is observed at the next lower concentration.

The last three compounds of the table are bacteriostats known in the art and are included to better illustrate the unusually high level of activity of the cinnamanalides of the present invention.

TABLE

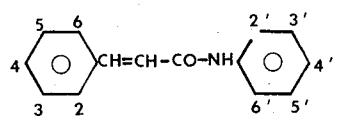

CINNAMANILIDE

| Compound No. | Radical Substituted in Cinnamanilide Position Number | | | | | | | | Compound Activity Without Soap | Compound Activity With Soap |
| --- | --- | --- | --- | --- | --- | --- | --- | --- | --- | --- |
|  | 2 | 3 | 4 | 5 | 2' | 3' | 4' | 5' |  |  |
| 1 |  |  |  | Cl |  | $CF_3$ | Cl |  | .12–.61 | .313–.625 |
| 2 |  |  |  | Br |  | $CF_3$ | Cl |  | .025–.12 | .31–.625 |
| 3 |  |  | Cl | Cl |  | $CF_3$ |  | $CF_3$ | <.025 | .156–.313 |
| 4 |  |  | Cl | Cl |  | $CF_3$ |  |  | .12–.61 | .156–.313 |
| 5 |  |  | Cl | Cl |  | $CF_3$ | Cl |  | <.025 | .078–.156 |
| 6 |  |  |  | Cl |  | $CF_3$ |  | $CF_3$ | <.025 | .078–.156 |
| 7 |  |  |  | Br |  | $CF_3$ |  |  | 3.1–5.4 | .625–1.25 |
| 8 |  |  |  | Br |  | $CF_3$ |  | $CF_3$ | <.025 | .313–.625 |
| 9 |  |  |  | Cl |  | $CF_3$ |  |  | .61–3.1 | .625–1.25 |
| 10 |  |  | Cl |  |  | $CF_3$ | Cl |  | >1920 | <.078 |
| 11 |  |  | Cl |  |  | $CF_3$ |  | $CF_3$ | >1920 | <.078 |
| 12 |  |  | Cl | Cl |  | $CF_3$ | Br |  | .025–.12 | .12–.61 |
| 13 |  |  | Cl | Cl |  |  | $OCF_3$ |  | .12–.61 | .12–.61 |
| 14 |  |  | Cl | Cl |  | $OCF_2CHF_2$ |  |  | .12–.61 | .61–1.25 |
| $C_1$ |  |  | Cl | Cl |  |  | Cl |  | >1920 | >20 |
| $C_2$ |  |  | Cl | Cl |  |  | $NO_2$ |  | >1920 | >20 |
| $C_3$ |  |  | Cl |  |  | $CF_3$ | Br |  | 384–1920 | >20 |
| $C_4$ |  |  | Cl |  | $CF_3$ |  | Cl |  | >1920 | >20 |
| $C_5$ |  |  |  |  |  | Cl | Cl |  | >1920 | >20 |
| $C_6$ |  |  | Cl |  |  | $CF_3$ |  |  | >1920 | >20 |
| $C_7$ |  |  |  |  |  | $CF_3$ | Cl |  | >1920 | >20 |
| $C_8$ |  |  |  |  |  | $CF_3$ |  |  | 3.1–15.4 | 2.5–5 |
| $C_9$ |  |  |  |  |  | $CF_3$ | Br |  | >1920 | >20 |
| $C_{10}$ |  |  |  |  |  | $CF_3$ | $CF_3$ |  | >1920 | >20 |
| $C_{11}$ |  |  | Cl |  |  | $OCF_2CHF_2$ |  |  | >1920 | >20 |
| 2,2'-Methylenebis(3,4,6-trichlorophenol) |  |  |  |  |  |  |  |  | .313–0.625 | .313–.625 |
| Tribromosalicylanilide |  |  |  |  |  |  |  |  | .313–.625 | .313–.625 |
| 2,2'-Methylenebis(3,4,6-trichlorophenol)di(N-methylcarbamate) |  |  |  |  |  |  |  |  | .313–.625 | .313–.625 |

By reference to the Table it is immediately apparent that the anti-microbial activity of the compound is strictly dependent upon the position of the substituents and compounds closely related to the compounds of the present invention but which are not substituted in the same manner as the compounds of the present invention, when tested in a similar manner, are found to be inactive.

EXAMPLE XVI

The following is illustrative of typical soap formulations which can be prepared using the substituted cinnamanilides of the present invention:

a. Two parts of finely ground substituted cinnamanilide of the present invention are blended well with 98 parts of soda soap filings. The blend is then milled thoroughly and pressed into molds. The soda soap may be of the LUX type described above or any other suitable bar soap stock.

b. One part of any one of the finely ground bacteriostatic substituted cinnamanilide compounds of this invention is carefully blended with one part of 3,4,4'-trichlorocarbanilide or with one part of hexachlorophene or with one part 3,4-dichloro-3-(trifluoromethyl)-carbanilide, or with one part of dibromosalicylanilide, or one part of tribromosalicylanilide or one part of a mixture of the latter two salicylanilides (Diaphene). This mixture is intimately milled with 98 parts of soda soap filings as above and pressed into molds.

The mixture of the bacteriostats can also be first blended with one to two parts of sodium lauryl sulfate, or "Igepon T", or "Triton 720", and the resulting mixture is then intimately milled with 97–96 parts of soda soap.

The dispersing or wetting agents are, in another modification of procedure, first dissolved or emulsified in a small amount of water, acetone, alcohol, etc. and then blended with the bacteriostats of this invention or their combinations with other bacteriostats, prior to incorporation into soap.

EXAMPLE XVII

A bacteriostatic dry cleaning agent is prepared by dissolving 0.5 g of any one of the claimed compounds in a blend of 5 g of ethanol or isopropanol and 5 g of a condensation product of nonylphenol with 15 moles of ethylene oxide and adding this solution to 89.5 g of tetrachloroethylene or trichloroethylene.

EXAMPLE XVIII

A bacteriostatic surface cleaner, especially for ceramics, bathtubs, metal containers etc. is prepared by mixing thoroughly 3 parts of any one of the claimed compounds of this invention, 5 parts of sodium dodecylbenzene sulfonate, 12 parts of calcined sodium carbonate, 1 part of sodium silicate, 3 parts of sodium tripolyphosphate and 76 parts of diaatmaceous earth.

EXAMPLE XIX

A bacteriostatic aerosol to be applied to surfaces as for instance wood, metal, floors, textiles or for air disinfection is prepared by filling an aerosol dispenser with a formulation consisting of 1 part of any one of the claimed compounds of this invention, 19 parts of isopropanol and 80 parts of a blend of Freon 11 and Freon 12 in a weight ratio of 1:2.

EXAMPLE XX

Bacteriostic fibers are prepared by dissolving a copolymer obtained from vinylidene chloride and acrylonitrile, in dimethylformamide (four to five times its weight). Any one of the compounds of this invention is added in an amount sufficient to produce a fiber by spinning which contains 0.5 to 2% of the bacteriostat uniformly distributed therein.

EXAMPLE XXI

A bacteriostatic mixture used for the production of various bacteriostatic coatings is prepared by dissolving 4 to 5 g of any one of the claimed compounds in 350 g of methyl ethyl ketone, adding 250 g of toluene and blending the aforesaid solution with 220 g of stabilized polyvinyl chloride and 22 g of dioctyl phthalate by agitation for 30 minutes.

EXAMPLE XXII

A bacteriostatic wound dusting powder is prepared by thoroughly mixing 75 g of talcum, 10 g of rice starch, 10 g of zinc oxide, 4 g of zinc stearate and 1 g of any of the compounds claimed in this invention. After passing through a sieve, the powder is again well mixed.

What is claimed is:

1. A compound of the formula

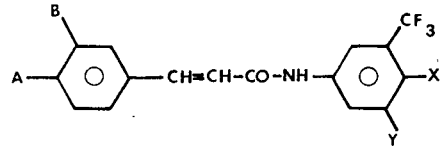

wherein:
A is selected from the group consisting of H and Cl;
B is selected from the group consisting of Cl and Br;
X is selected from the group consisting of H and Cl; and
Y is selected from the group consisting of H and $CF_3$;

2. A compound according to claim 1 wherein:
$A = B$ = chlorine;
$X$ = hydrogen;
$Y$ = trifluoromethyl.

3. A compound according to claim 1 wherein:
$A = B = X$ = chlorine
$Y$ = hydrogen.

4. A compound according to claim 1 wherein:
$A = X$ = hydrogen;
$B$ = chlorine;
$Y$ = trifluoromethyl.

5. A compound according to claim 1 wherein:
$A = X$ = hydrogen;
$B$ = bromine;
$Y$ = trifluoromethyl.

6. A compound according to claim 1 wherein:
$A = Y$ = hydrogen;
$B = X$ = chlorine.

7. A compound according to claim 1 wherein:
$A = Y$ = hydrogen;
$B$ = bromine;
$X$ = chlorine.

8. A compound according to claim 1 wherein:
$A = B$ = chlorine;
$X = Y$ = hydrogen.

9. A compound according to claim 1 wherein:
$A = X = Y$ = hydrogen;
$B$ = bromine.

10. A compound according to claim 1 wherein: $A = X = Y$ = hydrogen;
$B$ = chlorine.

11. A compound of the structure

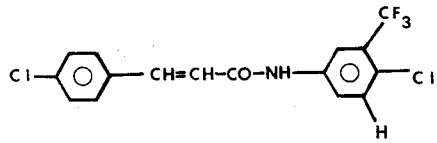

12. A compound of the structure

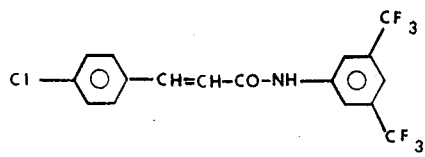
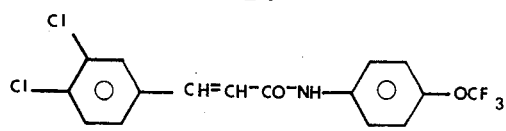
13. A compound of the structure
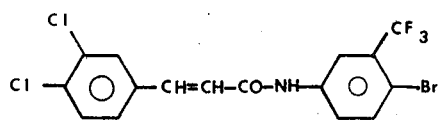
14. A compound of the structure
15. A compound of the structure
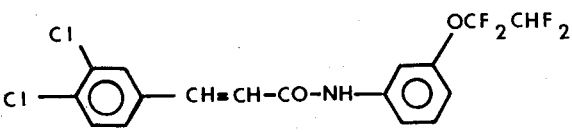
* * * * *